United States Patent [19]

Davis et al.

[11] Patent Number: 5,021,218
[45] Date of Patent: Jun. 4, 1991

[54] APPARATUS FOR TRANSPORTING SPECIMEN SLIDES

[75] Inventors: Richard E. Davis, Grand Rapids, Mich.; Michael D. Glant, Indianapolis, Ind.

[73] Assignee: DLP, Inc., Grand Rapids, Mich.

[21] Appl. No.: 467,484

[22] Filed: Jan. 19, 1990

[51] Int. Cl.⁵ .............. B01L 9/00; B01L 3/00; B65D 85/48; F24H 7/00
[52] U.S. Cl. .................. 422/104; 422/102; 206/456; 220/351
[58] Field of Search .............. 422/104, 99, 102; 206/456, 454, 449, 569; 220/351, 507, 676, 4.21; 73/863; 211/41; 118/500; 427/4

[56] References Cited

U.S. PATENT DOCUMENTS

| | | | |
|---|---|---|---|
| 3,362,564 | 1/1968 | Mueller | 220/346 |
| 3,379,303 | 4/1968 | Jenkins | 206/456 |
| 4,635,791 | 1/1987 | Jackson et al. | 206/456 |
| 4,731,335 | 3/1988 | Brigati | 436/63 |
| 4,801,431 | 1/1989 | Cuomo et al. | 422/104 |
| 4,844,284 | 7/1989 | Drozd et al. | 206/540 |

OTHER PUBLICATIONS

Fisher Scientific Cat., 1988, pp. 709-710, 716-719, 1441.

*Primary Examiner*—David L. Lacey
*Assistant Examiner*—Theresa A. Trembley
*Attorney, Agent, or Firm*—Barnes, Kisselle, Raisch, Choate, Whittemore & Hulbert

[57] ABSTRACT

An apparatus is provided to identify, index and display slides having a specimen thereon, and to secure the slides so as to protect biopsy material and similar specimens retained thereon. There is also provided a slide carrier to hold slides in spaced relation while slides are collectively immersed or wetted, thereby saving considerable time during the processing of the slides by laboratory personnel. The slides are marked by a permanent and unique code which is visible while the slides are retained within the slide carrier container.

9 Claims, 2 Drawing Sheets

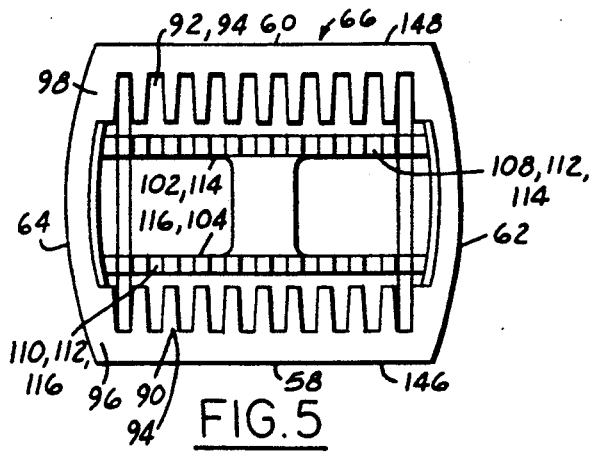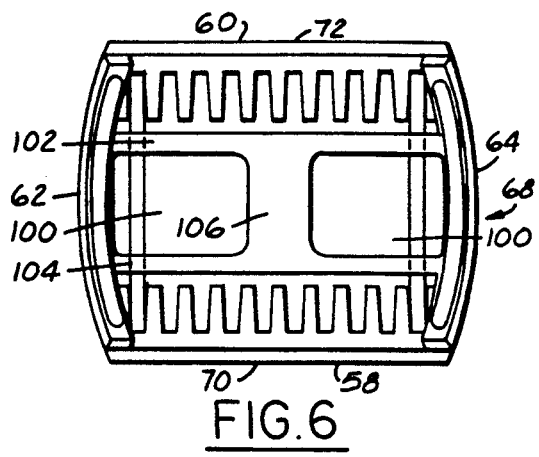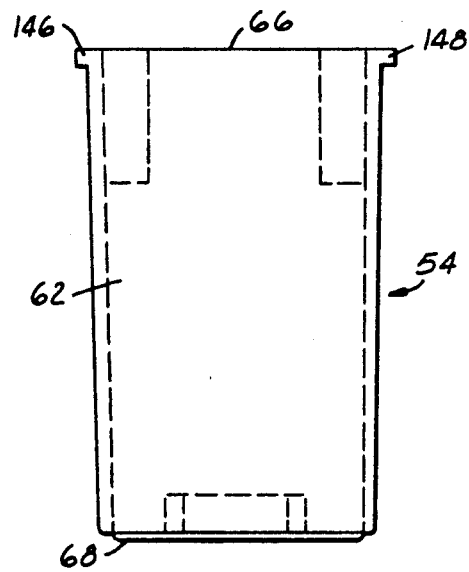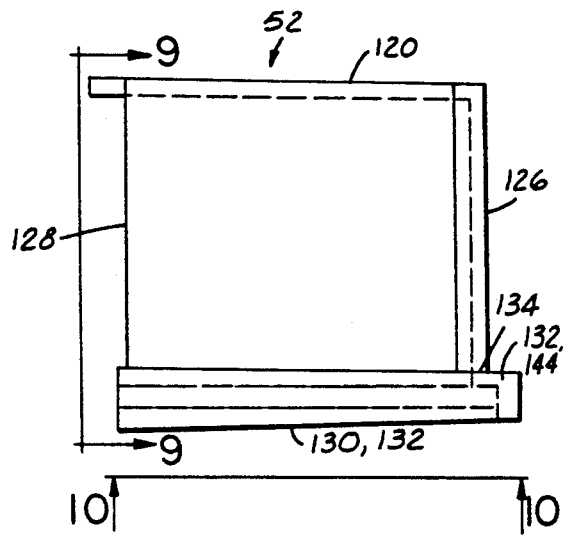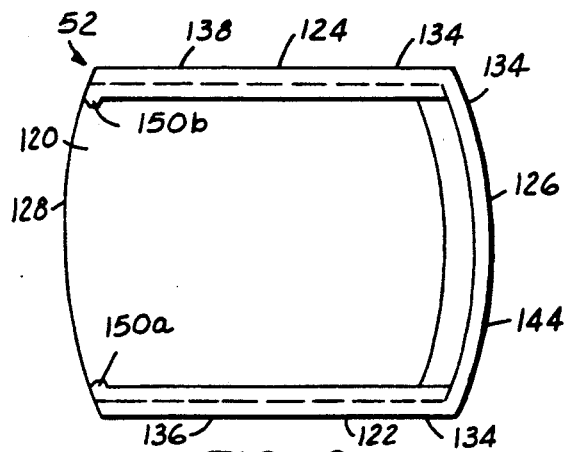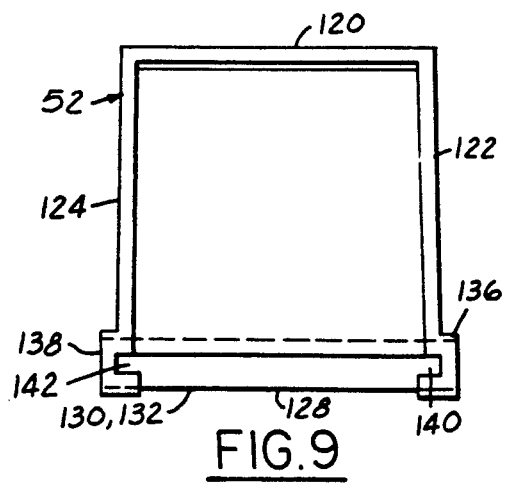

APPARATUS FOR TRANSPORTING SPECIMEN SLIDES

FIELD OF INVENTION

This invention relates to slides and slide containers constructed and adapted for identifying, indexing and displaying slides, and for securing said slides so as to protect biopsy material and similar specimens retained thereon.

BACKGROUND AND SUMMARY OF THE INVENTION

Specimens are placed on slides for analysis under a microscope and similar diagnostic devices. In the medical field specimens typically consist of biopsy material such as tissue or fluids.

Biopsy procedures are commonly done for thyroid, breast and lymph/salivary testing. The procedure is conducted to extract a specimen sample from a nodule or growth on the thyroid gland or lymph gland. Currently, fine hypodermic needles are used to extract a tissue (cell) or fluid sample from the nodule. The hypodermic needles consist of a needle attached to a syringe which comprises a barrel and plunger.

The procedure consists of: a) numbing the skin over the nodule with, for example, Lidocane; b) inserting the biopsy hypodermic needle into the nodule; c) drawing the plunger of the hypodermic syringe to create a vacuum; and d) aspirating or drawing the tissue or fluid sample under vacuum into the needle. The needle is then withdrawn from the patient and the plunger is depressed to deposit the specimen on a slide.

Typically several specimen samples are taken at numerous locations within and on the surface of the nodule. Therefore, several separate slides are used, one for each specimen. The specimen simply sticks to the slide. The slides having specimens may be air dried or coated with a solution or a preservative such as alcohol (ethanol or methanol). The slides are then transported to a laboratory location. The slides are removed and immersed in, or wetted with, a staining solution to enhance viewing under a microscope. The slides are placed in a suitable rack, held in spaced relation, until they are coverslipped and ready to be viewed.

The biopsy procedure is a delicate and difficult procedure therefore it is important to secure and protect the specimen derived therefrom. Kits are provided which may include all the apparatus needed to produce the specimens for transport on slides to the laboratory. It is important that the specimens derived during the delicate biopsy procedure be properly identified and transported to the lab in a secure and protective enclosure.

Slides are used in a number of fields besides the medical field, and there are a number of general methods available for storing slides. U.S. Pat. Nos. 3,235,068 and 3,379,303 describe slotted slide retainers of cardboard or plastic. The retainers include a slotted box with either a telescoping or sliding cover. In either case, tape or other means must be used to secure the cover. The slides are not identifiable when the cover is closed. U.S. Pat. Nos. 3,362,564 and 4,844,284 describe slidable covers. The 284 patent describes a "child-proof" cover having a skirt and latching number which engages the side member of a tray and which is released when the top of the cover is depressed.

In the medical field, currently, cardboard slide holders are generally used to retain, transport and store the slides. A typical slide holder consists of 2 pieces of flat cardboard continuously joined at the outer perimeter and having a series of slots cut into the top piece. Slides are inserted into the slots and a numeric or other code is written on the slide, to identify the specimen. A fold-over cover is generally used to protect the slides. If the slides are to be wetted, they are generally removed, wetted and placed on a drying rack.

It is desirable to have a more convenient and secure means for retaining and storing slides. It is also desirable to have a means to mark the slides, and to maintain the order of the slides and to protect the slides and specimens from damage. It is further desirable to have a convenient method for wetting the slides with the alcohol and staining solutions, and to have a suitable combination holder to retain the slides before final coverslipping.

Accordingly, it is an object of the invention to provide a permanent, convenient means for marking, identifying and indexing each slide having a specimen, and to effectively and conveniently index, retain and protect slides during procedures, transporting of slides, staining and wetting of slides and the coverslipping of slides. Other objects include providing a means for holding slides in spaced relation while slides are collectively immersed or wetted, thereby saving considerable time during the processing of the slides by laboratory personnel.

DETAILED DESCRIPTION OF THE DRAWINGS

FIG. 5 is a top view taken along line 5—5 of FIG. 4.

FIG. 6 is a bottom view taken along line 6—6 of FIG. 4.

FIG. 7 is a front view of the slide holder portion of the slide carrier.

FIG. 8 is a side view of the cap portion of the slide carrier.

FIG. 9 is a view taken along line 9—9 of FIG. 8.

FIG. 10 is a bottom view taken along line 10—10 of FIG. 8.

DETAILED DESCRIPTION OF THE INVENTION

Figure 1:
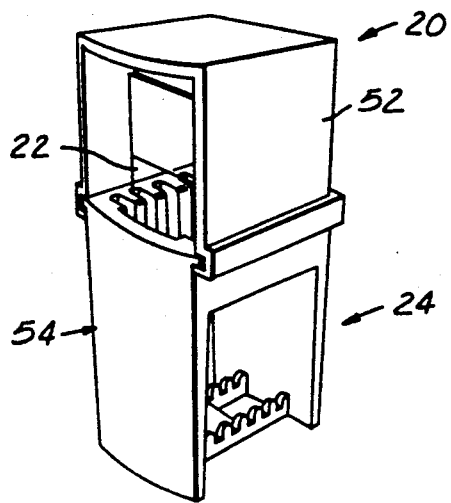
FIG. 1 is an isometric, perspective view of a slide and the slide carrier.
Figure 2:
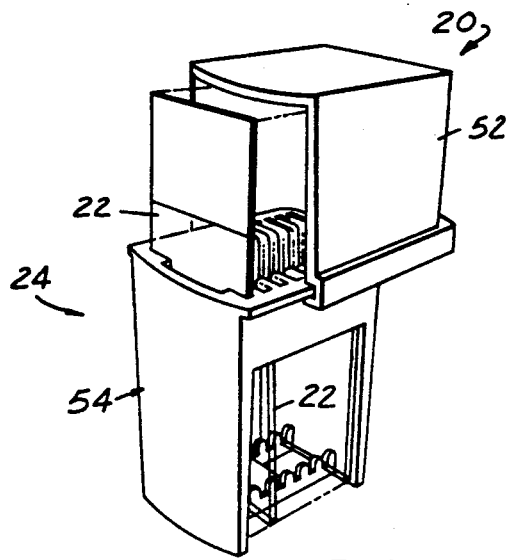
FIG. 2 is an isometric, perspective view of a slide and the slide carrier with the cap portion partially open.
Figure 3:
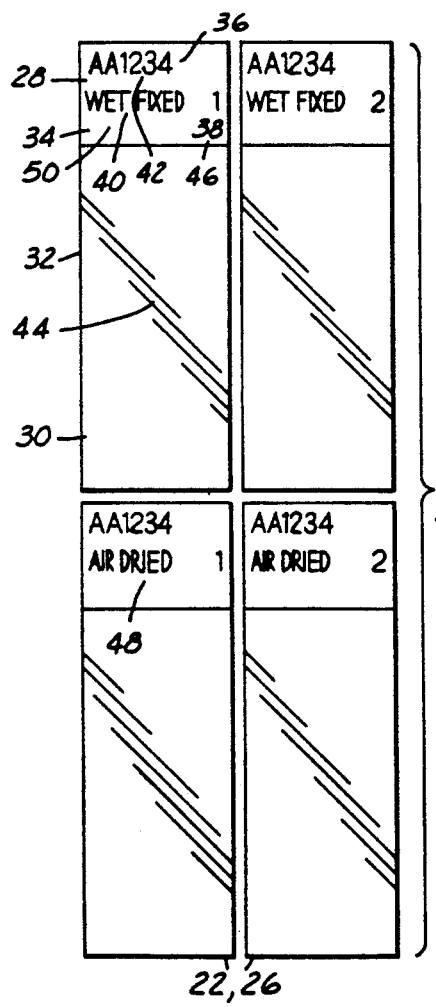
FIG. 3 is a plan view of slides marked with a set of codes.

Referring to FIGS. 1 and 2 there is shown the slide identification and transportation kit 20 comprising a plurality of slides 22 and slide carrier 24. As shown in FIG. 3, preferably slides 22 are coated slides 26, color coated at a top portion 28. Slides 22, 26 have a top portion 28, a bottom portion 30 and a mid portion 32. Preferably, colored coating 34 of slide 26 has permanently etched therein three sets of codes 36, 38, 40. First code 36 comprises an essentially unlimited set of alpha numeric characters 42 to identify an individual patient's specimen or sample 44. Each code 36 is unique to each patient's sample 44. The second set of codes 38 identifies the number 46 of the slide 22, 26. The third code 40 carries the designation, Air Dry Slide 48 or Wet Fix Slide 50.

Figure 4:
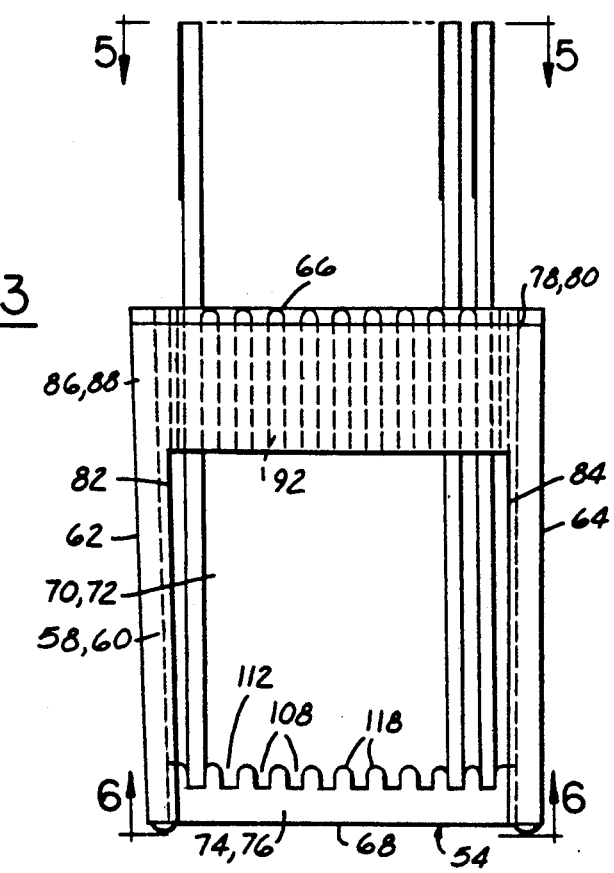
FIG. 4 is a side view of the slide holder portion of the slide carrier.

As shown in FIGS. 1 and 2, slides 22, 26 and slide carrier 24 are constructed and arranged to identify and display the codes 36, 38, 40. Slide carrier 24 generally comprises two portions, a cap 52 and a slide holder 54. Referring to FIGS. 4, 5 and 6 slide holder 54 has 4 sides, comprising side wall 58, side wall 60, front wall 62 and back wall 64, a top 66 and a base 68. The top 66 is constructed and arranged to releasably engage cap 52.

As shown in FIG. 4, side wall 58 has an opening 70 and side wall 60 has an opening 72. Openings 70 and 72 are identical, opposed openings, each of which extends from the base 68 of slide holder 54 so that the base 68 and the bottoms 74, 76 of side wall 58 and side wall 60 are completely open. The openings 70 and 72 extend from the base 68 and then up to sections 78 and 80 of side wall 58 and side wall 60 respectively, adjacent the top 66 of the slide holder 54. Each of openings 70 and 72 also extends transversely to respective points 82 and 84 adjacent front and back walls 62 and 64. The openings 70 and 72 form a partial side wall 86 and an opposed partial side wall 88 respectively. The partial side walls 86 and 88 expose the bottom portion 30 and preferably a part of the mid portion 32 of slide 22, 26. Front and back walls 62 and 64 (FIG. 7) are generally parallel to one another and are connected to and integral with side walls 58 and 60. Front and back walls 62 and 64 are each concave outward to provide added stability to slide holder 54.

Sections 78 and 80 each have a plurality of spaced apart slots 90, 92 formed by grooves 94 cut into the interior surfaces 96, 98 of side walls 58 and 60 respectively. The slots 90 in side wall 58 and the slots 92 in side wall 60 are opposed directly across from one another.

Referring to FIG. 6, base 68 has openings 100 which are in communication with openings 70 and 72 in side walls 58 and 60. Base 68 has a pair of parallel spaced apart beams 102 and 104 connected to front and back walls 62 and 64. Preferably, there is a lateral brace 106 connected between beams 102 and 104 to define the openings 100 and to provide added support. Beams 102 and 104 are preferably recessed with respect to the base 68. Beams 102 and 104 each have a plurality of spaced apart aligned slots 108, 110 (FIG. 5) formed by grooves 112 cut into the top surfaces 114, 116 of beams 102 and 104. The slots 108 of beam 102 and the slots 110 of beam 104 are aligned directly across from one another. The slots 108, 110 of beams 102, 104 are aligned with slots 90, 92 of side walls 58, 60. Slots 90, 92, 108 and 110 thereby cooperate to hold slides 22, 26 in parallel spaced apart relation. Further, the top, bottom and mid portions 28, 30 and 32 of slides 22, 26 are all maintained in spaced apart relation Preferably the sides 118 of slots 108, 110 are curved or rounded to facilitate the placing of slides 22, 26 into slots 90, 92, 108 and 110.

Referring to FIGS. 8, 9 and 10 cap 52 of slide carrier 24 has a top 120 and a side wall 122, side wall 124 and a rear wall 126 connected to one another and carried by the top 120. Cap 52 also has an open end 128 opposite rear wall 126. The bottom is open at 130. The rear wall 126 is concave outward.

A skirt section 132, surrounding the side and rear walls, extends outward from, and is carried by, side walls 122 and 124 and rear wall 126. The skirt section 132 is coextensive with, and is continuous around, the perimeter 134 of walls 122, 124, 126.

The skirt section 132 has a first section 136 and a second section 138 each of which has a U-shaped channel, thereby forming a pair of channels 140, 142, coextensive with respective side wall 122 and side wall 124, terminating at a third section 144 which is concave outward.

Cap 52 is releasably secured to slide holder 54 by engaging a pair of opposed flanges 146, 148 (FIGS. 5 and 7) at the top 66 of slide holder 54. Opposed flanges 146, 148 comprise first flange 146 which extends outwardly from side wall 58 and second flange 148 which extends outwardly from side wall 60 of slide holder 54. Channels 140, 142 of cap 52 are engaged with flanges 146, 148 of holder 54 to secure cap 52 to slide holder 54.

Desirably, either the first section 136 or the second section 138 of the skirt section 132 includes a tab 150. Tab 150 is disposed about 90° from the end of said section of skirt section 132 at the open end 128 of cap 52. Preferably, there are two tabs 150a, 150b, (FIG. 10), one at each respective section 136 and 138.

In use, the codes 36, 38 and 40 on slides 22, 26 are noted on a data sheet (not shown) which is transported with the slides having specimens to the lab.

The slide carrier 24 is then opened to expose the slides 22, 26 by releasing tabs 150a, 150b on cap 52. Cap 52 is then released from holder 54 by sliding the cap 52 along flanges 146, 148. A slide 22, 26 is removed, a specimen is deposited on the slide 22, 26, then the slide 22, 26 is returned to the holder 54. If desired, the location from which the specimen is taken may be noted on the data sheet along with the codes 36, 38, 40. The sequence is repeated as required. The cap 52 is then replaced on the holder 54 by sliding flanges 146, 148 into U-shaped channels 140, 142 until tabs 150a, 150b engage a front or back wall 62 or 64 of holder 54.

The Wet Fix Slides 50 may be wetted with alcohol or other solution by dipping slide carrier 24 into the solution or by depositing solution onto the slides 22, 26 through one or more openings 70, 72 or 100. At the lab, the slides 22, 26 may be wetted in a similar manner and left in the slide carrier 24 to dry until required for viewing or coverslipping. The slides 22, 26 may be left in the slide carrier 24 for permanent storage or further transportation.

Preferably, the top portion 28 of the slides 22 are coated with a colored coating 34 forming coated slides 26, and the codes 36, 38 and 40 are etched on the top portion 28 of the slides 26 by means of a laser. Slides 22 may also be identified by other means such as with a permanent ink or other marker.

We claim

1. A slide identification and transportation kit constructed and arranged to mark, identify, index and display a plurality of slides and specimens thereon and to secure and protect said slides and specimens comprising:

a slide carrier comprising a cap and slide holder constructed and arranged with internal slots to maintain said plurality of slides in spaced relation while exposing said plurality of slides to display said plurality of slides and to provide access to at least a bottom portion of said plurality of slides while securing and protecting said plurality of slides and specimens;

said slide holder comprising a front wall and an opposed back wall, connected by opposed side walls; said opposed side walls containing openings; an open top and a base connected to said front wall and said opposed back wall and a plurality of slots formed by grooves in one of either said opposed side walls or said base; and wherein each of said openings extending from the base of said holder to sections adjacent the top of said opposed side walls, and extending transversely to respective points adjacent said front wall and said opposed back wall; and said openings constructed and arranged to provide opposed partial side walls to provide access to a bottom portion and a mid portion of said plurality of slides.

2. The kit of claim 1 wherein said sections adjacent the top of said opposed side walls have a plurality of spaced apart slots formed by grooves cut into the interior surfaces of said sections, said slots in said opposed side walls constructed and arranged to be opposed directly across from one another to provide alignment of said plurality of slides in parallel spaced relation.

3. The kit of claim 2 wherein said base comprises:
an opening which communicates with said openings in said respective side walls;
a pair of parallel spaced apart beams connected to said front wall and said opposed back wall and recessed with respect to said base;
a plurality of spaced apart slots formed by grooves cut into a top surface of each of said respective beams, said slots on said respective beams aligned directly across from one another; and
said slots of said beams and said slots of said opposed side walls are aligned to provide alignment of said plurality of slides in parallel spaced relation from said top portion to said bottom portion of said plurality of slides.

4. The kit of claim 3 wherein said cap comprises:
side walls and a back wall connected to one another and carried by a top and having an open end opposite the back wall and an open base;
a skirt section constructed and arranged to extend outward from each of said side walls and said back walls of said cap and connected to said side walls and said back wall of said cap and coextensive with said side walls and said back wall of said cap around the perimeter of said side walls and said back wall of said cap; and
said skirt section comprising a first section and a second section each having a U-shaped channel forming a pair of channels coextensive with each of said side walls of said cap, terminating at a third section.

5. The kit of claim 4 wherein said cap is releasably secured to said slide holder by engaging a pair of opposed flanges at the top of said opposed side walls of said holder with the U-shaped channels of said cap.

6. The kit of claim 5 wherein said cap comprises a pair of tabs, one on the end of each of said pair of channels at said open end of said cap, to bear upon one of said front wall and said opposed back wall of said holder when said cap is slidably secured to said holder, said cap and said holder constructed and arranged to secure and protect said plurality of slides and to provide access to the top, mid and bottom portions of said plurality of slides.

7. The kit of claim 6 wherein said front wall and said opposed back wall of said holder, said back wall of said cap and said third section of said skirt are each concave outward, and said base of said holder comprises a lateral brace between said beams to provide added support and stability to said slide carrier.

8. The slide identification and transportation kit of claim 4, 5, 6 or 7 and further comprising slides having at least one permanent identifying code at the top portion of each of said slides, said code comprising a plurality of characters permanently applied onto said top portion to identify each of said slides and specimens.

9. The slide identification and transportation kit of claim 4, 5, 6 or 7 and further comprising slides having a colored coating at the top portion of each of said slides and at least one code comprising a plurality of characters permanently laser etched into said coating to identify each of said slides and specimens.

* * * * *